United States Patent [19]

Hwan et al.

[11] Patent Number: 5,354,912
[45] Date of Patent: Oct. 11, 1994

[54] METHOD FOR THE REMOVAL OF DIMETHYL ETHER FROM METHYL TERTIARY BUTYL ETHER

[75] Inventors: Rei-Yu J. Hwan, Houston; Charles J. Kruse, Cypress, both of Tex.

[73] Assignee: Texaco Chemical Company, White Plains, N.Y.

[21] Appl. No.: 69,482

[22] Filed: Jun. 1, 1993

[51] Int. Cl.$^5$ .................... C07C 41/06; C07C 41/09; C07C 41/34
[52] U.S. Cl. .................... 568/697; 568/699; 568/698; 568/922
[58] Field of Search ................ 368/697, 698, 699, 922

[56] References Cited

U.S. PATENT DOCUMENTS 5,243,091  9/1993  Kruse .................... 568/697

Primary Examiner—Howard T. Mars
Attorney, Agent, or Firm—James L. Bailey; Kenneth R. Priem; Carl G. Ries

[57] ABSTRACT

An isobutylene feed mixture comprising MTBE, isobutylene and methanol is passed through an isobutylene conversion zone to form an isobutylene conversion product comprising unreacted methanol, unreacted isobutylene, dimethyl ether, MTBE and water, then charged to a countercurrent methanol extraction zone and contacting with water to provide an overhead raffinate comprising isobutylene, MTBE and water, and an extract comprising methanol, water, MTBE, isobutylene and dimethyl ether;

the extract is distilled to provide a vaporized overhead fraction comprising MTBE, isobutylene, methanol, and dimethyl ether;

the vaporized overhead fraction is partially condensed and from about 5 to 10 wt. % of the mixed phase condensate is vented to thereby provide a liquid condensate that is substantially free from dissolved dimethyl ether, and the condensate is recycled to the methanol extraction zone.

10 Claims, 1 Drawing Sheet

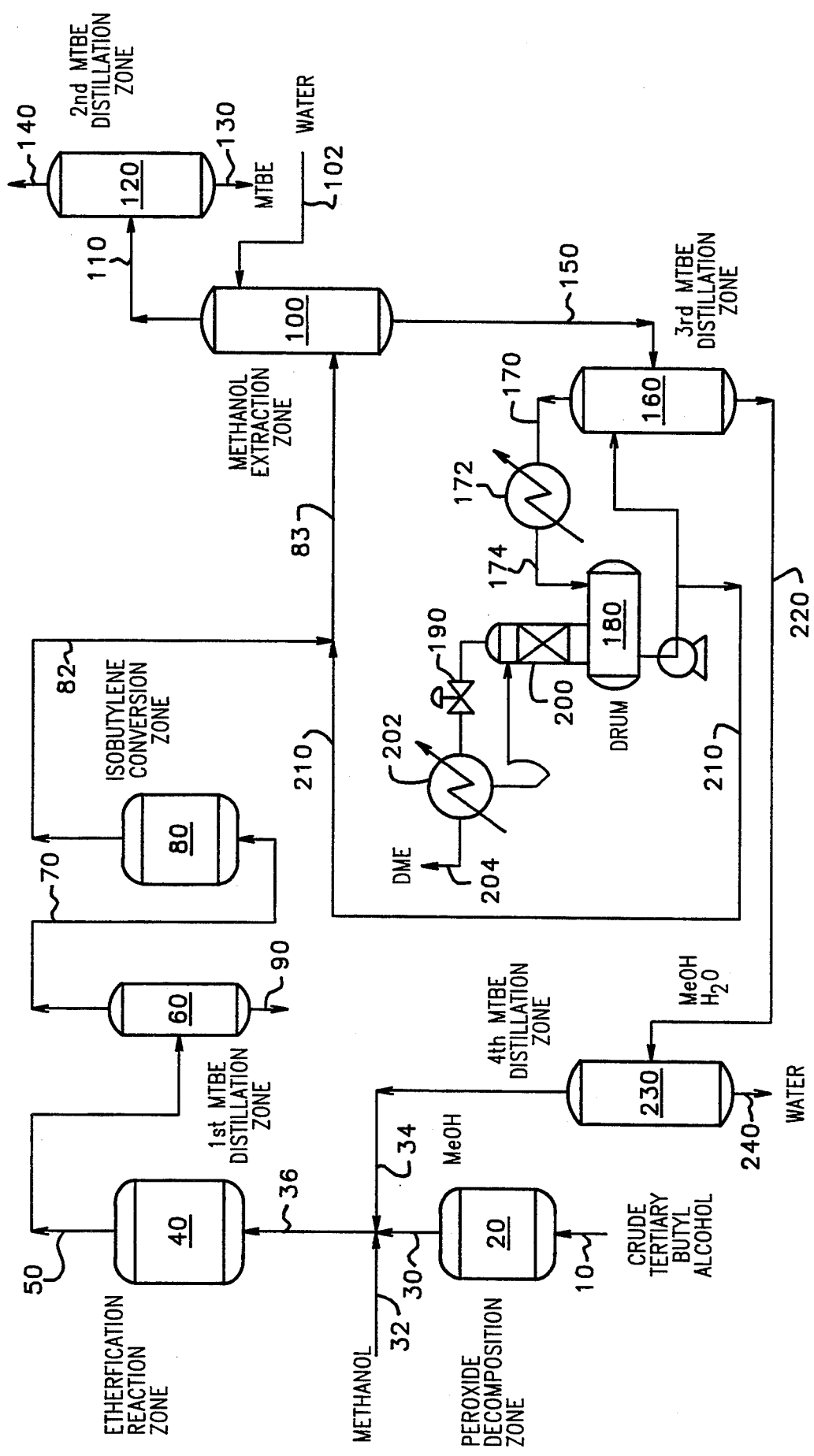

METHOD FOR THE REMOVAL OF DIMETHYL ETHER FROM METHYL TERTIARY BUTYL ETHER

BACKGROUND OF THE INVENTION

1. Technical Field of the Invention

This invention relates to a method for the manufacture and purification of methyl tertiary butyl ether. More particularly, this invention relates to a method for the manufacture of methyl tertiary butyl ether from tertiary butyl alcohol, isobutylene and methanol and for the purification of the methyl tertiary butyl ether formed by the reaction. Still more particularly, this invention relates to a method for the manufacture of methyl tertiary butyl ether from tertiary butyl alcohol, isobutylene and methanol and for an improvement in the purification of the methyl tertiary butyl ether formed by the reaction in the removal of dimethyl ether formed during the reaction.

2. Prior Art

The preparation of methyl tert-butyl ether from methyl and tert-butyl alcohols is discussed in S. V. Rozhkov et al., Prevrashch Uglevodorodov, Kislotno-Osnovn. Geterogennykh Katal. Tezisy Dokl., Vses. Konf., 1977, 150 (C. A. 92:58165y). Here the TBA and methanol undergo etherification over KU-2 strongly acidic sulfopolystyrene cation-exchangers under mild conditions. This reference contains data on basic parameters of such a process.

In U.S. Pat. No. 4,144,138 (1979) to Rao et al., there is disclosed a method for recovering methyl tertiary butyl ether from an etherification reaction effluent by azeotropic distillation to recover a methanol-ether azeotrope overhead which is water-washed to give pure ether raffinate, the latter being azeotropically distilled to yield ether-methanol overhead which is recycled to water washing.

Copending Kruse et al. U.S. patent application Ser. No. 07/978,570, filed Nov. 19, 1992 and entitled "METHOD FOR THE MANUFACTURE AND RECOVERY OF METHYL TERTIARY BUTYL ETHER (D# 81,086)" discloses a method for the preparation of methyl tertiary butyl ether wherein tertiary butyl alcohol is reacted with methanol to provide a reaction product comprising methyl tertiary butyl ether and by-product isobutylene and wherein the by-product isobutylene is reacted with methanol to provide additional methyl tertiary butyl ether and also a method for the purification of the methyl tertiary butyl ether.

Trubac U.S. Pat. No. 4,814,517 discloses a modified method for the purification of methyl tertiary butyl ether manufactured from methanol and isobutylene wherein a distillate overhead stream obtained during the purification of the methyl tertiary butyl ether is passed in liquid phase sequentially through a bed of silica gel to removal methanol and a bed of a zeolite molecular sieve to remove dimethyl ether.

Background Information

Methyl tertiary butyl ether (MTBE) is finding increasing use as a blending component in high octane gasoline as the current gasoline additives based on lead and manganese are phased out. Commercial processes have been developed for the manufacture of methyl tertiary butyl ether are based upon the liquid-phase reaction of isobutylene (IBE) and methanol (MEOH) catalyzed by a cationic ion-exchange resin.

With the expanding use of MTBE as an acceptable gasoline additive, a growing problem is the availability of raw materials. Historically, the critical raw material is isobutylene (Oil and Gas J., Jun. 8, 1987, p. 55). It would be advantageous, therefore, to have a process to make MTBE that does not require isobutylene as a building block. It would be advantageous to have an efficient process for making MTBE by reaction of methanol with tertiary butyl alcohol, since tertiary butyl alcohol (TBA) is readily available commercially through isobutane oxidation.

It is known to react methanol with tertiary butyl alcohol in the presence of a catalyst in order to produce methyl tertiary butyl ether. A wide variety of catalysts have been suggested for this purpose.

In U.S. Pat. No. 2,282,469 to Frolich there is disclosed a process for preparing methyl tertiary butyl ether over a catalyst comprising Kieselguhr impregnated with phosphoric acid at a temperature of about 175° F. to 350° F.

Japanese Patent 0007432 teaches the use of zeolites to make dialkyl ethers containing primary or secondary alkyl groups. The zeolites have a porous structure and are represented by:

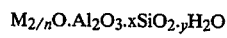

$$M_{2/n}O \cdot Al_2O_3 \cdot xSiO_2 \cdot yH_2O$$

where M is an alkali metal or alkaline earth metal cation or organic base cation, n is the valence of the cation and x and y are variables.

U.S. Pat. No. 4,058,576 to Chang et al. teaches the use of (pentasil-type) aluminosilicate zeolites, such as ZSM-5, having a pore size greater than 5 angstrom units and a silica-to-alumina ratio of at least 12, to convert lower alcohols to a mixture of ethers and olefins.

In U.S. Pat. No. 4,822,921 there is disclosed a method for producing MTBE by reacting tertiary butyl alcohol and methanol in the presence of a catalyst comprising an inert support, such as titania, having a phosphoric acid impregnated thereon.

U.S. Pat. No. 4,827,048 discloses a method for producing MTBE by reacting tertiary butyl alcohol and methanol in the presence of a catalyst comprising a heteropoly acid such as 12-tungstophosphoric acid or 12-molybdophosphoric acid on an inert support, such as titania.

Two of the principal by-products formed during the reaction of the methanol with the tertiary butyl alcohol are water and isobutylene. Methanol and MTBE form an azeotrope which is broken only with difficulty and therefore the separation of methanol from MTBE during the recovery of purified tertiary methyl butyl ether presents a serious problem.

In U.S. Pat. No. 4,820,877, separation of methanol from MTBE is accomplished by using a refinery fuel gas to enhance the separation of methanol into the overhead stream of a distillation column.

In U.S. Pat. No. 4,814,517, separation of methanol from MTBE is accomplished by using a silica gel to preferentially adsorb methanol from an MTBE stream and by periodically regenerating the silica gel.

In U.S. Pat. No. 4,798,674, separation of methanol from MTBE is accomplished by using a membrane of crosslinked polyvinyl alcohol or a quaternary ammonium ion resin. Methanol preferentially permeates through the membrane increasing the MTBE concentration of the charge liquid.

In U.S. Pat. No. 4,759,850, separation of methanol from MTBE is accomplished by reverse osmosis.

In U.S. Pat. No. 4,440,963, separation of methanol from MTBE is accomplished by adding an agent such as 2-methyl pentane or Freon 113 to forman azeotrope with methanol. This azeotrope is recovered overhead giving a methanol-free MTBE bottoms product.

As recognized by Rao et al. in U.S. Pat. No. 4,144,138, isobutylene is formed as a by-product when methanol is reacted with tertiary butyl alcohol. In accordance with the Rao process, the isobutylene is separated from the reaction product in an initial azeotropic distillation step as a noncondensable gas. Rao teach that the part of the isobutylene may be flashed from the reaction product for recycle, depending upon purity.

SUMMARY OF THE INVENTION

In accordance with the present invention, a process is provided wherein by-product isobutylene formed when methanol is reacted with tertiary butyl alcohol is further reacted downstream of the tertiary butyl alcohol etherification reaction zone is an isobutylene conversion zone with methanol to form a reaction product comprising methyl tertiary butyl ether and dimethyl ether and wherein the methyl tertiary butyl ether formed by the reactions is purified by the removal of impurities, including dimethyl ether.

Thus, the present invention is directed to a method for the manufacture and purification of methyl tertiary butyl ether which comprises the steps of:

a. Continuously reacting methanol with tertiary butyl alcohol in a tertiary butyl alcohol etherification reaction zone containing a bed of an etherification catalyst to form a tertiary butyl alcohol reaction product comprising methanol, unreacted tertiary butyl alcohol, water, isobutylene and methyl tertiary butyl ether, b. Continuously charging the tertiary butyl alcohol reaction product to a primary methyl tertiary butyl ether recovery distillation zone and separating it therein into a lighter methanol and isobutylene-containing methyl tertiary butyl ether distillation fraction comprising methyl tertiary butyl ether, isobutylene and methanol and a second heavier distillation fraction comprising methanol, tertiary butyl alcohol and water, c. Continuously charging the methanol and isobutylene-containing methyl tertiary butyl ether distillation fraction to an isobutylene conversion reaction zone and contacting it therein with a solid resin etherification catalyst to thereby convert isobutylene and methanol to methyl tertiary butyl ether and form a methyl tertiary butyl ether product stream containing contaminating quantities of dimethyl ether, methanol and isobutylene, d. Continuously charging the methyl tertiary butyl ether product stream to a methanol solvent extraction zone and countercurrently contacting it therein with water to provide a raffinate comprising isobutylene and methyl tertiary butyl ether and a bottoms extract comprising residual methyl tertiary butyl ether, methanol, dimethyl ether and water, e. Continuously charging the raffinate to a second methyl tertiary butyl ether purification distillation zone and separating it therein into a third lighter distillation fraction comprising isobutylene and water and a fourth heavier distillation fraction consisting essentially of methyl tertiary butyl ether, f. Continuously charging the aqueous extract to a third methyl tertiary butyl ether distillation zone and separating it therein into a fifth lighter distillation fraction comprising methyl tertiary butyl ether, methanol, isobutylene, dimethyl ether and water and a sixth heavier distillation fraction comprising methanol and water, g. Continuously charging the sixth distillation fraction to a fourth methanol recovery distillation zone and separating it therein into a seventh lighter distillation fraction comprising methanol and an eighth heavier distillation fraction comprising water, h. Continuously charging the fifth lighter distillation fraction, as a mixed liquid and vapor, to an accumulator, or drum, and venting from the drum a vapor by-product comprising dimethyl ether and isobutylene, and i. Recycling the liquid portion of the fifth lighter distillation fraction to said methanol solvent extraction zone.

The Tertiary Butyl Alcohol Feedstock

Tertiary butyl alcohol can be produced by the thermal or catalytic decomposition of tertiary butyl hydroperoxide. Tertiary butyl alcohol formed in this fashion will normally contain a minor Mount of peroxide contaminants such as tertiary butyl hydroperoxide, ditertiarybutyl peroxide, allyl tertiary butyl peroxide, etc. Normally, the peroxide contaminants in the tertiary butyl alcohol will remain as contaminants in the etherification reaction zone reaction product.

In accordance with the present invention, the peroxides-contaminated tertiary butyl alcohol is charged to a peroxide decomposition reaction zone where the peroxide contaminants are thermally or catalytically decomposed to form a tertiary butyl alcohol feedstock that is substantially free from peroxide contaminants. Contaminating quantities of decomposition products such as acetone and methyl formate will normally be present.

When the peroxides are to be thermally decomposed, the peroxides-contaminated tertiary butyl alcohol feedstock is continuously passed through a peroxides decomposition reactor under thermal decomposition conditions including a temperature of about 100° to about 200° C., a pressure of about 80 to about 500 psia and a flow rate of about 0.5 to about 20 volumes of feedstock per reactor volume per hour to thereby provide a substantially peroxides-free tertiary butyl alcohol reaction product.

Alternately, the peroxide contaminants may be catalytically decomposed.

A wide variety of catalysts may be used for this purpose, such as cobalt borate as disclosed in U.S. Pat. No. 4,547,598, a nickel, copper, chromia catalyst as disclosed in Sanderson et al. U.S. Pat. No. 4,704,482, an iron, copper, chromia, cobalt catalyst as disclosed in Sanderson et al. U.S. Pat. No. 4,705,903, a base treated hydrogenation catalyst from groups VIB or VIIIB of the Periodic Table as disclosed in Sanderson et al. U.S. Pat. No. 4,742,179, a nickel, copper, chromium and barium catalyst as disclosed in Sanderson et al. U.S. Pat. No. 4,873,380, a metal phthalocyanine catalyst as disclosed in Sanderson et al. U.S. Pat. No. 4,910,349, an imidazole-promoted methyl metal phthalocyanine catalyst as disclosed in Sanderson et al. U.S. Pat. No. 4,912,266, a base promoted metal phthalocyanine catalyst as disclosed in Sanderson et al. U.S. Pat. No. 4,912,267, a solid ruthenium catalyst as disclosed in Sanderson et al. U.S. Pat. No. 4,922,033, a promoted metal porphine catalyst as disclosed in Sanderson et al. U.S. Pat. No. 4,922,034, etc.

The conversion conditions to be utilized in the catalytic peroxide decomposition zone may comprise, for example, a temperature of about 100° to about 200° C., a pressure of about 80 to about 500 psia and a space velocity of about 0.5 to about 20 volumes of feed per volume of catalyst per hour.

DETAILED DESCRIPTION OF THE PRESENT INVENTION

The Tertiary Butyl Alcohol Etherification Reaction Catalyst

In accordance with the MTBE manufacture and purification method of the present invention, a tertiary butyl alcohol etherification reaction zone containing a bed of etherification catalyst is utilized. A wide variety of etherification catalysts can be used for this purpose, such as Kieselguhr impregnated with phosphoric acid as disclosed in Frolich U.S. Pat. No. 2,282,469, zeolites as disclosed in Japanese Patent 0007432, aluminosilicate zeolites as disclosed in Chang et al. U.S. Pat. No. 4,058,576, titania having phosphoric acid impregnated thereon as disclosed in Knifton U.S. Pat. No. 4,822,921, a hetero polyacid such as 12-tungstophosphoric acid or 12-molybdophosphoric acid supported on titania, etc.

A preferred catalyst is a sulfonic acid resin etherification catalyst such as a sulfonated polystyrene resin crosslinked with divinyl benzene. Thus, the catalyst may comprise a strongly acidic ion exchange resin consisting essentially of sulfonated polystyrene, such as a divinyl benzene crosslinked polystyrene matrix containing from about 0.5 to about 20% of copolymerized divinyl benzene. Resins of this nature are manufactured and sold commercially under various trade names such as "Dowex 50", "Nalcite HCR" and "Amberlyst 15". The use of catalysts of this nature is disclosed, for example, in Rao U.S. Pat. No. 4,144,138.

The reaction conditions to be utilized when reacting methanol with tertiary butyl alcohol in the presence of an etherification catalyst of the type disclosed in the prior art include a reaction temperature of about 90° to about 140° C., a pressure of about 30 to about 500 psia and a space velocity of about 0.5 to about 20 volumes of feed per volume of etherification catalyst per hour.

The Solid Resin Etherification Catalyst

In accordance with the present invention, a distillate fraction obtained during the recovery process, identified above as a methanol and isobutylene-containing methyl tertiary butyl ether distillation fraction, and which contains isobutylene, methanol and methyl tertiary butyl ether is brought into contact with a solid resin isobutylene etherification catalyst in order to convert a significant portion of the isobutylene and methanol to methyl tertiary butyl ether.

Any suitable solid resin etherification catalyst may be used for this purpose, such as a strongly acidic ion exchange resin consisting essentially of sulfonated polystyrene, such as a divinyl benzene crosslink polystyrene matrix containing from about 0.5 to about 20% of copolymerized divinyl benzene. Resins of this nature are manufactured and sold commercially under various tradenames such as "Dowex 50", "Nalcite HCR" and "Amberlyst 15". The use of catalyst of this nature is disclosed, for example, in Rao U.S. Pat. No. 4,144,138.

The methanol and isobutylene-containing methyl tertiary butyl ether distillation fraction will normally contain from about 5 to about 10 wt. % of isobutylene, and from about 70 to about 80 wt. % of methyl tertiary butyl ether and from about 10 to about 20 wt. % of methanol. The feedstock for the isobutylene conversion reaction zone may comprise the methanol and isobutylene-containing methyl tertiary butyl ether distillation fraction which may be used alone, or in admixture with additional isobutylene added from another source (e.g., isobutylene recovered from the third lighter distillation fraction).

The methanol and isobutylene-containing methyl tertiary butyl ether distillation fraction, or isobutylene feedstock is brought into contact with a solid resin isobutylene etherification catalyst in the isobutylene conversion reaction zone under conversion conditions including, for example, a temperature of about 35° to about 130° C., a pressure of about 30 to about 500 psia and a space velocity of about 0.5 to about 20 volumes of feedstock per volume of etherification catalyst per hour. As a consequence, an isobutylene conversion product is formed which will normally contain from about 0 to about 10 wt. % of isobutylene, about 75 to about 85 wt. % of methyl tertiary butyl ether and from about 10 to about 15 wt. % of methanol. The isobutylene conversion product will also contain contaminating quantities of dimethyl ether (e.g., from about 0.5 to about 5.0 wt. % of dimethyl ether).

BRIEF DESCRIPTION OF THE DRAWING

The drawing is a schematic flow sheet with conventional parts omitted showing the general reaction and recovery sequence of the present invention for the manufacture and purification of methyl tertiary butyl ether.

DESCRIPTION OF THE PREFERRED EMBODIMENT

Turning now to the drawing, there is shown a schematic flow sheet illustrating the preferred method for the practice of the process of the present invention. In the drawing, conventional parts, such as valves, pumps, temperature control sensors, pressure sensors, heaters, coolers, flow control regulation apparatus, reflux condenses, reboilers, etc., have been omitted.

In accordance with a preferred embodiment of the present invention, a peroxides-contaminated, or "crude" tertiary butyl alcohol feed is charged by way of line 10 to a peroxide decomposition reaction zone 20 where thermal peroxide decomposition conditions are established, including a temperature of about 100° to about 200° C., a pressure of about 80 to about 500 psia and a flow rate of about 0.5 to about 20 volumes of feedstock per reactor volume per hour to thereby provide a substantially peroxides-free tertiary butyl alcohol reaction product that is discharged from the peroxide decomposition zone 20 by a discharge line 30.

The peroxides-free decomposition reaction product discharged from the peroxide decomposition zone 30 will typically have a composition as follows:

TABLE 1

| PEROXIDE REACTION ZONE DECOMPOSITION PRODUCT | |
|---|---|
| Component | % |
| TBA[1] | 97.4 |
| Water | 0.02 |

TABLE 1-continued

| PEROXIDE REACTION ZONE DECOMPOSITION PRODUCT | |
|---|---|
| Component | % |
| Other[2] | 2.6 |

[1] Tertiary butyl alcohol
[2] Acetone, tertiary butyl formate, isopropyl alcohol, etc.

In accordance with the present invention, there is provided an etherification reaction zone 40 containing a bed of a solid etherification catalyst. A preferred catalyst is a sulfonic acid resin etherification catalyst such as a sulfonated polystyrene resin crosslinked with divinyl benzene (e.g., a strongly acidic ion exchange resin consisting essentially of sulfonated polystyrene, such as a divinyl benzene crosslinked polystyrene matrix containing from about 0.5 to about 20% of copolymerized divinyl benzene, such as a strongly acidic ion exchange resin manufactured and sold commercially under the tradename "Dowex 50", "Nalcite HCR" or "Amberlyst 15").

Alternately, other catalysts known to those skilled in the art may be used, such as a fluorophosphoric acid-on-titania catalyst prepared in the manner described in Knifton et al. U.S. Pat. No. 4,822,921 by treating titania extrudates, such as extrudates having a surface area of about 50 m[2]/g, with an acetone solution of fluorophosphoric acid to provide as a catalyst, titania having about 3.0 wt. % of phosphorus and about 0.6 wt. % of fluorine deposited thereon and bonded thereto by a calcining treatment.

A tertiary butyl alcohol feed mixture is charged to the etherification reaction zone 40 by the line 36; the feed mixture 36 comprising substantially peroxides-free tertiary butyl alcohol charged by the line 30, fresh methanol charged by the line 32 and recycle methanol charged by a recycle line 34. Methanol is charged to the feed line 36 through methanol charge lines 32 and 34 in an amount such that the molar ratio of methanol to tertiary butyl alcohol is within the range of about 1.1 to about 4:1 and, more preferably, from about 1.5 to about 2.5:1 and, still more preferably, in the ratio of about 2 moles of methanol per mole of tertiary butyl alcohol. It will be understood that tertiary butyl alcohol prepared by the thermal or catalytic decomposition of tertiary butyl hydroperoxide will contain minor amounts of impurities such that, for example, the feedstock charged to the reaction zone 40 through the feed line 36 will contain the following components:

TABLE 2

| ETHERIFICATION REACTION ZONE FEED MIXTURE | |
|---|---|
| Component | % |
| Methanol | 40.5 |
| TBA[1] | 46.7 |
| Acetone | 0.5 |
| 2-Propanol | 5.7 |
| MTBE[2] | 0.2 |
| DTBP[3] | 0.03 |
| t-Butyl Formate | 0.2 |
| Water | 5.9 |

[1] Tertiary butyl alcohol
[2] Methyl tertiary butyl ether
[3] Ditertiary butyl peroxide It will be understood that trace amounts of other peroxides such as tertiary butyl hydroperoxide, tertiary allyl peroxide, etc., may also be present.

Within the etherification reaction zone 40, the tertiary butyl alcohol feed mixture is brought into contact with the bed of etherification catalyst under reaction conditions including a temperature of about 30° C. to about 200° C., and more preferably from about 80° to about 140° C., and still more preferably from about 90° to about 130° C. and a pressure of about 30 to about 500 psia, and more preferably from about 200 to about 300 psia. Space velocities within the etherification reaction zone are suitably such that about 0.5 to about 20 volumes of feed mixture per volume of etherification catalyst per hour are fed to the etherification reaction zone 40 and, more preferably from about 1 to about 4 volumes of feed mixture per volume of etherification catalyst per hour.

Within the etherification reaction zone 40, methanol will exothermally react with the tertiary butyl alcohol to form methyl tertiary butyl ether which will be contained in a tertiary butyl alcohol reaction product discharged from the etherification reaction zone 40 by way of a line 50 leading to a first methyl tertiary butyl ether (MTBE) distillation zone 60.

As a specific example, when the solid etherification catalyst is a sulfonic acid resin such as Amberlyst 15 and when the molar ratio of methanol to tertiary butyl alcohol in the feed mixture charged to the etherification reaction zone 40 by the line 36 is about 2 moles of methanol per mole of tertiary butyl alcohol, and the reaction is conducted at a temperature of about 100° C. at a feed rate of about 2 volumes of feed mixture per volume of catalyst per hour, the etherification reaction product may have the composition shown by the following table:

TABLE 3

| ETHERIFICATION REACTION PRODUCT | |
|---|---|
| Component | % |
| Water | 14.0 |
| Methanol | 27.8 |
| Isobutylene | 3.0 |
| TBA[1] | 14.1 |
| MTBE[2] | 34.5 |
| Other[3] | 6.8 |

[1] Tertiary butyl alcohol
[2] Methyl tertiary butyl ether
[3] Includes the acetone, propanol, ditertiary butyl peroxide, tertiary butyl formate, etc. initially present in the tertiary butyl alcohol feedstock.

The tertiary butyl alcohol etherification reaction product charged to the primary distillation zone 60 by way the charge line 50 is fractionated therein under distillation conditions including a liquid reflux temperature of about 30° to about 100° C., and more preferably about 40° to about 80° C., a reboiler temperature of about 80° to about 115° C., and more preferably from about 95° to about 105° C., and a pressure of about 15 to about 60 psia, the distillation condition being selected such that substantially all of the MTBE in the etherification reaction product 50 is taken overhead from the first distillation zone 60 by a line 70. As a consequence, the first distillation fraction 70 taken overhead from the distillation zone 60 will comprise substantially all of the isobutylene and substantially all of the methyl tertiary butyl ether and some of the methanol charged to the first distillation zone 60. The second heavier distillation fraction 90 discharged from the first MTBE distillation zone 60 will comprise methanol, tertiary butyl alcohol and water.

In accordance with the present invention, the methanol and isobutylene-containing methyl tertiary butyl ether distillation fraction 70 is charged to an isobutylene conversion zone 80 containing a bed of solid resin etherification catalyst such as a bed of Amberlyst 15 sulfonated polystyrenedivinyl benzene copolymer acidic ion exchange resin. If desired, additional isobutylene may be charged to the isobutylene conversion zone 80 from a suitable source, not shown, such as isobutylene recovered from the distillate fraction 140, which is obtained in a manner to be described; the additional isobutylene comprising about 2 to 15 wt. % of the weight of the first distillation fraction 70.

Etherification reaction conditions established in the isobutylene conversion zone 80 include, for example, a temperature of about 35° to about 130° C., and more preferably from about 40° to about 70° C., a pressure of about 50 to about 500 psia, and more preferably from about 150 to about 250 psia, and a space velocity of about 0.5 to about 4 volumes of isobutylene feed mixture per volume of solid resin etherification catalyst per hour. As a consequence, a portion of the methanol and isobutylene contained in the first distillation fraction 32 will be converted to methyl tertiary butyl ether. Typically, the conversion will amount to about 30 to about 40 wt. %, based on the isobutylene. By-product dimethyl ether will also be formed.

An isobutylene conversion product is discharged from the isobutylene conversion zone 80 by a line 82 leading to a methanol solvent extraction zone 100. The composition of a typical isobutylene conversion product may be as follows:

TABLE 4

| ISOBUTYLENE CONVERSION PRODUCT | |
|---|---|
| Component | % |
| Isobutylene | 5.4 |
| MTBE | 79.5 |
| Methanol | 12.2 |
| Dimethyl Ether | 1.6 |
| Other | 1.3 |

In accordance with the present invention, the isobutylene conversion product 82 is charged to a methanol solvent extraction zone 100 together with a MTBE recycle stream 210, obtained in a manner to be described, where it is counter-currently contacted with water introduced into the solvent extraction zone 100 by a charge line 102.

Within the methanol solvent extraction zone 100, solvent extraction conditions are established for countercurrent solvent extraction including a ratio of water to isobutylene conversion product within the range of about 0.1 to about 0.3 parts of water per part of isobutylene conversion product per hour, and more preferably include a ratio of water to isobutylene conversion product within the range of about 0.1 to about 0.2 parts of water per part of isobutylene conversion product per hour. Extraction conditions may suitably include a temperature of about 20° to about 60° C., and more preferably from about 30° to about 40° C., and a pressure of about 50 to about 500 psia, and more preferably from about 50 to about 150 psia.

As a consequence, a supernatant raffinate 110 will be formed which is withdrawn from the methanol solvent extraction zone 100 by line 110 leading to a second MTBE purification distillation zone 120. The aqueous extract is discharged from the solvent extraction zone 100 by way of a bottoms discharge line 150 leading to a third methyl tertiary butyl ether distillation zone 160.

Within the second methyl tertiary butyl ether purification distillation zone 120, distillation conditions are established including a liquid reflux temperature of about 30° to about 60° C., and more preferably from about 40° to about 55° C., a reboiler temperature of about 100° to about 140° C., and more preferably from about 125° to about 135° C. and a pressure of about 70 to about 120 psia, and more preferably from about 90 to about 110 psia, to thereby form a lighter distillation fraction 140, comprising isobutylene and water discharged from the second distillation zone 120 by a line 140 and a heavier fourth distillation fraction 130 consisting essentially of product, namely methyl tertiary butyl ether.

The third distillation fraction 140 will comprise a mixture of isobutylene and water and may be processed in any desired manner. For example, it may be charged to a decantation zone (not shown) where it can settle to form a supernatant isobutylene phase and a water phase. If desired, all or a part of the supernatant isobutylene phase may be recycled to the isobutylene conversion zone 80.

The extract 150 charged to the third distillation zone 160 will comprise methyl tertiary butyl ether, methanol isobutylene, dimethyl ether and water. For example, the composition of the extract 150 may be as follows:

TABLE 5

| EXTRACT | |
|---|---|
| Component | % |
| Isobutylene | 1.2 |
| MTBE | 7.2 |
| Methanol | 33.3 |
| Dimethyl Ether | 3.0 |
| Water | 54.4 |
| Other | 0.9 |

Although dimethyl ether has a specific gravity of only 0.661, a boiling point of −24.5° and a flash point of −42° C., as shown in Table 5, it is concentrated and remains dissolved in the heavier extract stream 150. Within the third distillation column 160 distillation conditions are established, such as a reflux temperature of about 40° to about 70° C., and more preferably from about 55° to about 65° C., and a reboiler temperature of about 80° to about 120° C., and more preferably from about 105° to about 125° C., and a pressure of about 40 to about 45 psia to form a fifth lighter vaporized distillation fraction 170 comprising methyl tertiary butyl ether and a sixth heavier distillation fraction 220 comprising water and methanol. For example, the composition of the overhead stream 170 and the bottoms stream 220 may be as follows:

TABLE 6

| Component | Overhead % | Bottoms % |
|---|---|---|
| Isobutylene | 8.0 | 0.0 |
| MTBE | 53.0 | 0.0 |
| Dimethyl Ether | 15.0 | 0.0 |
| Acetone | 2.0 | 0.0 |
| Methanol | 21.0 | 35.0 |
| Water | 0.2 | 64.0 |
| Other | 0.8 | 1.0 |

In accordance with the present invention, the vaporized overhead fraction 170 is passed through a suitable cooling means, such as a heat exchanger 172 where it is cooled to a liquefaction temperature of about 40° to about 70° C. and is then charged by line 174 to an accumulator, or drum, 180. The drum is maintained at a temperature of about 40° to about 80° C. (e.g., 50° C.)

and a pressure of about 35 to about 45 psia (e.g., 38 psia). The drum 180 is provided with a rectifier 200 fitted with a throttling control valve 190 and a heat-exchange zone 202 which may suitably be maintained at a temperature of about −2° C. with a refrigerant such as propylene. During operations, the throttling valve 190 on the rectifier 200 is actuated so as to permit controlled venting of a portion of the vapor fraction 174 sufficient to permit all of the dimethyl ether to pass into the rectifier. The vapors, after passing through the valve 190 are cooled to a temperature of about −5° to about 0° C. in the heat exchange zone 202, so that most of the vapors will liquify and drain back into the drum 180 as condensate. However, all of the dimethyl ether and only a minor amount of isobutylene will be discharged from the rectifier 200 through the vent line 204 constituting about 5 to about 10 wt. % of the condensate.

As an example, about 1000 parts per hour of an extract having the composition shown in Table 5 may be fractionated in the column 160 to provide about 322 parts per hour of a vaporized overhead fraction 170 having the composition set forth in Table 6 and about 850 parts per hour of a bottoms fraction 220 having the composition set forth in Table 6. The vaporized overhead fraction 170, after partial liquefaction in the heat exchanger 172 is charged by line 174 to the drum 180. About 175 parts per hour of the partially liquified fraction 170 are returned to the column 160 as reflux and about 125 parts per hour of the partially liquified fraction 170 is returned by the line 210 to the methanol extraction zone 100. About 22 parts per hour of vapors are vented from the rectifier 200 through the vent line 204 and will comprise about 84 wt. % dimethyl ether, about 11 wt .% of isobutylene and about 5 wt. % other.

The sixth heavier distillation fraction 220 is charged to a fourth methanol distillation zone 230 where it is fractionated under distillation conditions which may suitably include a liquid reflux temperature of about 30° to about 80° C., and more preferably from about 60° to about 75° C., a reboiler temperature of about 100° to about 140° C., and more preferably from about 110° to about 120° C., and a pressure of about 15 to about 60 psia, and more preferably from about 20 to about 30 psia, into a lighter methanol distillation fraction 34 which may be suitably charged to the line 36 to the tertiary butyl alcohol etherification reaction zone 40. A heavier distillation fraction 240 consisting essentially of water is discharged from the fourth methanol distillation zone 230 by way of a line 240 and may be discharged from the system.

EXAMPLES

The invention will be further illustrated by the following specific examples which are given by way of illustration, and not as limitations on the scope of this invention. Where parts are mentioned, they are parts by weight.

In accordance with a preferred embodiment of the present invention, a tertiary butyl alcohol feedstock is continuously charged to the peroxides decomposition zone 20 by a line 10 where it is thermally treated under peroxide decomposition conditions including a temperature of about 100° to about 200° C., a pressure of about 80 to about 500 psia and a space velocity of about 0.5 to 4 volumes of feedstock per reactor volume per hour to thereby provide a substantially peroxides-free tertiary butyl alcohol product.

The peroxides-contaminated feedstock and substantially peroxides-free reaction product discharged from the peroxide decomposition zone 20 will typically have compositions as follows:

TABLE 7

| PEROXIDE DECOMPOSITION ZONE FEED AND PRODUCT | | |
|---|---|---|
| Component | Feed (Wt. %) | Product (Wt. %) |
| DTBP[1] | 0.87 | 0.02 |
| TBA[2] | 97.2 | 97.4 |
| Water | 0.1 | 0.02 |
| Other[3] | 1.8 | 2.6 |

[1]Ditertiary butyl peroxide
[2]Tertiary butyl alcohol
[3]Includes acetone, tertiary butyl formate isopropyl alcohol, etc.

The substantially peroxides-free tertiary butyl alcohol reaction product 30 is charged together with methanol from lines 32 and 34 to the tertiary butyl alcohol etherification reaction zone 40 in amounts such that about 2 moles of methanol are charged per mole of tertiary butyl alcohol.

Within the tertiary butyl alcohol etherification reaction zone 40, the feed mixture is passed through a bed of a suitable etherification catalyst such as Amberlyst 15 under reaction conditions, as described above, to provide a reaction product 50, having for example, the following composition.

TABLE 8

| ETHERIFICATION REACTION ZONE REACTION PRODUCT | |
|---|---|
| Component | Wt. % (Approx.) |
| Methanol | 27.6 |
| TBA | 14.1 |
| Water | 14.0 |
| Isobutylene | 3.0 |
| MTBE | 34.5 |
| Acetone | 0.4 |
| 2-Propanol | 6.0 |

The etherification zone reaction product 50 is discharged from the etherification reaction zone 40 by a line 50 leading to first methyl tertiary butyl ether distillation zone 60 where fraction 50 is separated into a lighter distillation fraction 70 comprising about 6.5 wt. % isobutylene, about 16.5 wt. % methanol and about 75 wt. % MTBE and a second heavier fraction 90 comprising about 37 wt. % methanol, about 26.0 wt. % tertiary butyl alcohol, about 26 wt. % water, about 11 wt. % isopropanol and about 0.5 wt. % of other contaminants.

The first distillation fraction 70 is continuously charged to an isobutylene conversion zone 80 through the line 70 and brought into contact therein with a solid resin etherification catalyst, such as Amberlyst 15, under conversion conditions as described above to form an isobutylene conversion product which is discharged from the isobutylene reaction zone 80 by a line 82 and which has the following composition:

TABLE 9

| ISOBUTYLENE CONVERSION PRODUCT | | |
|---|---|---|
| Component | Feed Wt. % (Aprox) | Product Wt. % (Approx) |
| Isobutylene | 11 | 5.5 |
| MTBE | 71 | 80 |
| Methanol | 15 | 12 |

TABLE 9-continued

ISOBUTYLENE CONVERSION PRODUCT

| Component | Feed Wt. % (Aprox) | Product Wt. % (Approx) |
|---|---|---|
| Other[1] | 3 | 3 |

[1]Includes dimethyl ether, acetone, 2-propanol carbon monoxide and water.

The isobutylene conversion product 82 and the recycle fraction 210 are continuously charged by way of a charge line 83 to the methanol extraction zone 100 in an amount such that the ratio of water to feedstock 83 is about 0.1 to about 0.3 part of water per part of feed mixture 83. Within the methanol extraction zone 100, the methanol is extracted from the isobutylene conversion product under extraction conditions as described above to thereby provide an overhead raffinate fraction 110 comprising isobutylene and methyl tertiary butyl ether and an extract 150, such as an extract having the composition given in Table 5.

The raffinate is fed by a line 110 to a second methyl tertiary butyl ether purification distillation zone 120 where it is resolved by distillation into a third lighter distillation fraction 140 comprising isobutylene and water and into a fourth heavier distillation fraction 130 consisting essentially of methyl tertiary butyl ether which is discharged as product.

Within the third distillation column 160 the extract is resolved under distillation conditions as set forth above into a fifth lighter distillation vaporized overhead fraction 170 comprising methyl tertiary butyl ether and a sixth heavier distillation fraction 220 comprising water and methanol.

In accordance with the present invention, the vaporized overhead fraction 170 is passed through a suitable cooling means, such as a heat exchanger 172 where it is partially liquified and then charged to a drum 180. The drum 180 is provided with a rectifier 200 fitted with a throttling control valve 190 and a heat-exchange zone 202. Controlled venting of a portion of the vapor fraction 174 is established sufficient to permit substantially all of the dimethyl ether to pass into the rectifier.

Having thus described our invention, what is claimed is:

1. A method for the continuous preparation and purification of methyl tertiary butyl ether which comprises the steps of:
   (a) continuously passing an isobutylene feed mixture comprising methyl tertiary butyl ether, isobutylene and methanol through an isobutylene conversion zone containing a bed of an etherification catalyst under etherification reaction conditions to form an isobutylene conversion reaction product comprising unreacted methanol, unreacted isobutylene, dimethyl ether, methyl tertiary butyl ether, carbon monoxide and water,
   (b) continuously charging said etherification conversion product to a methanol extraction zone and counter-currently contacting it therein with water to provide an overhead raffinate comprising isobutylene, methyl tertiary butyl ether and water, and an extract comprising methanol, water, methyl tertiary butyl ether, isobutylene and dimethyl ether,
   (c) continuously charging the raffinate to a raffinate distillation column and separating it therein into a lighter distillation fraction comprising isobutylene and water and a heavier distillation fraction consisting essentially of methyl tertiary butyl ether,
   (d) continuously charging said extract to an extract distillation column and separating it therein into a vaporized overhead fraction comprising methyl tertiary butyl ether, isobutylene, methanol and dimethyl ether; and a heavier distillation fraction comprising water and methanol,
   (e) continuously partially condensing said vaporized overhead fraction and then venting uncondensed vapors, constituting from about 5 to 10 wt. % of the resultant condensate to thereby provide a liquid overhead distillation fraction comprising methyl tertiary butyl ether, methanol and isobutylene that is substantially free from dissolved dimethyl ether and carbon monoxide, and
   (f) recycling said liquid overhead distillation fraction to said methanol extraction zone.

2. A method as in claim 1 wherein the distillation conditions established in the extract distillation column include a reflux temperature of about 40° to about 70° C., a reboiler temperature of about 80° to about 125° C. and a pressure of about 40 to 45 psia.

3. A method as in claim 1 wherein the distillation conditions established in the extract distillation column include a reflux temperature of about 55° to about 65° C., a reboiler temperature of about 105° to about 125° C. and a pressure of about 40 to 45 psia.

4. A method for the continuous preparation and purification of methyl tertiary butyl ether which comprises the steps of:
   (a) continuously passing an isobutylene feed mixture comprising methyl tertiary butyl ether, isobutylene and methanol through an isobutylene conversion zone containing a bed of an etherification catalyst under isobutylene conversion conditions to form an isobutylene conversion reaction product comprising unreacted methanol, unreacted isobutylene, dimethyl ether, methyl tertiary butyl ether and water,
   (b) continuously charging said isobutylene conversion product to a methanol extraction zone and countercurrently contacting it therein with water to provide an overhead raffinate comprising isobutylene, methyl tertiary butyl ether and water and an extract comprising methanol, water, methyl tertiary butyl ether, isobutylene and dimethyl ether,
   (c) continuously charging the raffinate to a raffinate distillation column and separating it therein into a lighter distillation fraction comprising isobutylene and water and a heavier distillation fraction consisting essentially of methyl tertiary butyl ether,
   (d) continuously charging said extract to an extract distillation column and separating it therein into a vaporized overhead fraction comprising methyl tertiary butyl ether, isobutylene, methanol and dimethyl ether; and a heavier distillation fraction comprising water and methanol,
   (e) continuously partially condensing said vaporized overhead fraction and then venting from about 5 to 10 wt. % of the condensate to thereby provide a liquid overhead distillation fraction comprising methyl tertiary butyl ether, methanol and isobutylene that is substantially completely free from dissolved dimethyl ether,
   (f) recycling said liquid overhead distillation fraction to said methanol extraction zone, (g) said feed mixture being reacted in said isobutylene conversion reaction zone under reaction conditions including a temperature of about 35° to about 130° C., a pressure of about 50 to 500 psia and a flow rate of about 0.5 to about 4 volumes of reaction mixture per volume of catalyst per hour, and (h) said isobutylene conversion product being countercurrently contacted with water in the methanol extraction zone in the ratio of about 0.1 to about 0.3 parts of water per part of isobutylene conversion product under extraction conditions including a temperature of about 20° to about 60° C. and a pressure of about 50 to 500 psia.

5. A method as in claim 4 wherein the distillation conditions established in the extract distillation column include a reflux temperature of about 40° to about 70° C., a reboiler temperature of about 80° to about 125° C. and a pressure of about 40 to 45 psia.

6. A method as in claim 4 wherein the distillation conditions established in the extract distillation column include a reflux temperature of about 55° to about 65° C., a reboiler temperature of about 105° to about 125° C. and a pressure of about 40 to 45 psia.

7. A method for the continuous preparation and purification of methyl tertiary butyl ether which comprises the steps of:

(a) continuously passing a tertiary butyl alcohol feed mixture comprising tertiary butyl alcohol and methanol through a tertiary butyl alcohol etherification reaction zone containing a bed of an etherification catalyst under etherification reaction conditions to form a primary tertiary butyl alcohol etherification reaction product comprising unreacted methanol, unreacted tertiary butyl alcohol, isobutylene, methyl tertiary butyl ether and water, (b) continuously charging said primary tertiary butyl alcohol etherification reaction product to a primary distillation column and separating it therein into a lighter isobutylene and methanol-containing methyl tertiary butyl ether distillation fraction and a heavier distillation fraction comprising tertiary butyl alcohol, methanol and water, (c) continuously passing said isobutylene and methanol-containing methyl tertiary butyl ether distillation fraction through an isobutylene conversion zone containing a bed of an etherification catalyst under isobutylene conversion reaction conditions to form an isobutylene conversion product comprising unreacted methanol, tertiary butyl alcohol, unreacted isobutylene, dimethyl ether, methyl tertiary butyl ether and water, (d) continuously charging said isobutylene conversion product to a methanol extraction zone and countercurrently contacting it therein with water to provide an overhead raffinate comprising isobutylene, methyl tertiary butyl ether and water, and an extract comprising methanol, water, methyl tertiary butyl ether, isobutylene and dimethyl ether, (e) continuously charging said raffinate to a raffinate distillation column and separating it therein into a lighter distillation fraction comprising isobutylene and water and a heavier distillation fraction consisting essentially of methyl tertiary butyl ether, (f) continuously charging said extract to an extract distillation column and separating it therein into a vaporized overhead fraction comprising methyl tertiary butyl ether, isobutylene, methanol, dimethyl ether and carbon monoxide, and a heavier distillation fraction comprising water and methanol, (g) continuously cooling said vaporized overhead fraction to a temperature of about 40° to about 80° C. to form a mixed phase condensate and collecting said condensate in a drum provided with a vent line, (h) maintaining said condensate in said drum at a temperature of about 40° to about 80° C., (i) venting from about 5 to 10 wt. % of the condensate in said drum and passing said vapors through said vent line, (j) cooling said vaporized condensate in said vent line to a temperature of about −5° to about 0° C. to at least partially liquify isobutylene, methanol and methyl tertiary butyl ether contained therein, (k) returning said liquified vapors to said drum, (l) venting residual vapors consisting essentially of dimethyl ether, carbon monoxide and isobutylene to thereby provide a liquid overhead distillation fraction comprising methyl tertiary butyl ether, methanol and isobutylene that is substantially completely free from dissolved dimethyl ether and carbon monoxide, and (m) recycling said liquid overhead distillation fraction to said methanol extraction zone.

8. A method as in claim 7 wherein the tertiary butyl alcohol feed mixture is reacted in said tertiary butyl alcohol etherification reaction zone under reaction conditions including a temperature of about 30° to about 200° C., a pressure of about 30 to 500 psia and a flow rate of about 1 to about 4 volumes of reaction mixture per volume of catalyst per hour, wherein lighter isobutylene distillation fraction is reacted in said isobutylene conversion zone under reaction conditions including a temperature of about 35° to about 130° C., a pressure of about 50 to 500 psia and a flow rate of about 0.5 to about 4 volumes of reaction mixture per volume of catalyst per hour, and said isobutylene etherification reaction product is countercurrently contacted with water in the methanol extraction zone in the ratio of about 0.1 to about 0.3 parts of water per part of etherification reaction product under extraction conditions including a temperature of about 20° to about 60° C. and a pressure of about 50 to 500 psia.

9. A method as in claim 8 wherein the distillation conditions established in said extract distillation column include a reflux temperature of about 40° to about 70° C., a reboiler temperature of about 80° to about 125° C. and a pressure of about 40 to 45 psia.

10. A method as in claim 8 wherein the distillation conditions established in the extract distillation column include a reflux temperature of about 55° to about 65° C., a reboiler temperature of about 105° to about 125° C. and a pressure of about 40 to 45 psia.

* * * * *